(12) United States Patent
Suzuki et al.

(10) Patent No.: US 9,422,519 B2
(45) Date of Patent: Aug. 23, 2016

(54) BIOMASS HYDROTHERMAL DECOMPOSITION SYSTEM AND SACCHARIDE-SOLUTION PRODUCTION METHOD USING BIOMASS MATERIAL

(75) Inventors: Hideo Suzuki, Tokyo (JP); Yoshio Kuromi, Tokyo (JP); Yoshitaka Kimura, Tokyo (JP)

(73) Assignee: MITSUBISHI HITACHI POWER SYSTEMS ENVIRONMENTAL SOLUTIONS, LTD., Yokohama-shi (JP)

(*) Notice: Subject to any disclaimer, the term of this patent is extended or adjusted under 35 U.S.C. 154(b) by 0 days.

(21) Appl. No.: 13/203,848

(22) PCT Filed: Jul. 9, 2010

(86) PCT No.: PCT/JP2010/061724
§ 371 (c)(1),
(2), (4) Date: Aug. 30, 2011

(87) PCT Pub. No.: WO2012/004894
PCT Pub. Date: Jan. 12, 2012

(65) Prior Publication Data
US 2012/0009642 A1    Jan. 12, 2012

(51) Int. Cl.
*C12M 1/00* (2006.01)
*C12P 7/10* (2006.01)
(Continued)

(52) U.S. Cl.
CPC *C12M 29/24* (2013.01); *C12P 7/10* (2013.01); *C12P 19/02* (2013.01); *C12P 19/14* (2013.01); *C13K 1/02* (2013.01); *C12P 2201/00* (2013.01); *Y02E 50/16* (2013.01)

(58) Field of Classification Search
CPC ........ C12P 2201/00; C12P 7/10; C12M 29/24
See application file for complete search history.

(56) References Cited

U.S. PATENT DOCUMENTS

| 3,985,728 A | 10/1976 | Lin |
| 4,023,982 A | 5/1977 | Knauth |

(Continued)

FOREIGN PATENT DOCUMENTS

| CA | 2660990 A1 | 8/2009 |
| CA | 2666152 A1 | 4/2010 |

(Continued)

OTHER PUBLICATIONS

Machine Translation of JP 2006-136263.*

(Continued)

*Primary Examiner* — Jonathan Hurst
(74) *Attorney, Agent, or Firm* — Westerman, Hattori, Daniels & Adrian, LLP

(57) ABSTRACT

A biomass hydrothermal decomposition system includes a hydrothermal decomposition unit 17 that transports the fed biomass material from a lower side to an upper side in an apparatus body 13 by screw means 14, feeds pressurized hot water 15 from an upper side different from a feed position of the biomass material 11 into the apparatus body 13, which is pressurized hot water to be discharged, so as to separate a lignin component and a hemicellulose component from the biomass material; a biomass solid discharging unit 18 that discharges a biomass solid 20 from the upper side of the apparatus body 13; and a slurrying vessel 21 communicating with the biomass solid discharging unit 18, into which water 19 is injected and the discharged biomass solid 20 is added to obtain a slurried biomass solid are provided.

6 Claims, 9 Drawing Sheets

(51) Int. Cl.
*C12P 19/02* (2006.01)
*C12P 19/14* (2006.01)
*C13K 1/02* (2006.01)

(56) References Cited

U.S. PATENT DOCUMENTS

| | | | |
|---|---|---|---|
| 4,152,197 A | 5/1979 | Lindahl et al. | |
| 4,384,897 A * | 5/1983 | Brink | 127/37 |
| 4,650,689 A | 3/1987 | Hedrick | |
| 4,746,401 A | 5/1988 | Roberts et al. | |
| 4,822,737 A * | 4/1989 | Saida | 435/162 |
| 4,859,322 A | 8/1989 | Huber | |
| 5,348,871 A | 9/1994 | Scott et al. | |
| 5,411,594 A | 5/1995 | Brelsford | |
| 5,424,417 A | 6/1995 | Torget et al. | |
| 5,466,108 A | 11/1995 | Piroska | |
| 6,022,419 A | 2/2000 | Torget et al. | |
| 6,419,788 B1 | 7/2002 | Wingerson | |
| 8,123,864 B2 | 2/2012 | Christensen et al. | |
| 8,163,517 B2 * | 4/2012 | Genta et al. | 435/41 |
| 8,728,770 B2 | 5/2014 | Ishikawa et al. | |
| 9,102,956 B2 | 8/2015 | Genta et al. | |
| 2007/0231869 A1 | 10/2007 | Holmgren et al. | |
| 2007/0259412 A1 | 11/2007 | Belanger et al. | |
| 2008/0026431 A1 * | 1/2008 | Saito | C12P 7/10 435/105 |
| 2008/0032344 A1 | 2/2008 | Fallavollita | |
| 2008/0044891 A1 | 2/2008 | Kinley et al. | |
| 2008/0299628 A1 | 12/2008 | Hallberg et al. | |
| 2010/0041119 A1 * | 2/2010 | Christensen et al. | 435/162 |
| 2010/0108567 A1 | 5/2010 | Medoff | |
| 2010/0184176 A1 | 7/2010 | Ishida et al. | |
| 2010/0269990 A1 | 10/2010 | Dottori et al. | |
| 2010/0285574 A1 | 11/2010 | Genta et al. | |
| 2010/0317843 A1 | 12/2010 | Sudhakaran et al. | |
| 2010/0330638 A1 | 12/2010 | Aita et al. | |
| 2011/0003348 A1 | 1/2011 | Genta et al. | |
| 2011/0079219 A1 | 4/2011 | McDonald et al. | |
| 2011/0314726 A1 | 12/2011 | Jameel et al. | |
| 2012/0006320 A1 | 1/2012 | Nguyen | |
| 2012/0009642 A1 | 1/2012 | Suzuki et al. | |
| 2012/0315683 A1 | 12/2012 | Mosier et al. | |
| 2013/0122555 A1 | 5/2013 | Suzuki et al. | |
| 2014/0004571 A1 | 1/2014 | Garrett et al. | |
| 2014/0273127 A1 | 9/2014 | Fuchs et al. | |

FOREIGN PATENT DOCUMENTS

| | | | |
|---|---|---|---|
| CA | 2 750 754 A1 | 1/2012 | |
| CA | 2654306 C | 10/2013 | |
| EP | 0 098 490 A2 | 1/1984 | |
| JP | 9-507386 A | 7/1997 | |
| JP | 11-506934 A | 6/1999 | |
| JP | 2002-059118 A | 2/2002 | |
| JP | 2003-311141 A | 11/2003 | |
| JP | 2004-105855 A | 4/2004 | |
| JP | 2005-27541 A | 2/2005 | |
| JP | 2005-168335 A | 6/2005 | |
| JP | 2005-205252 A | 8/2005 | |
| JP | 2005-229821 A | 9/2005 | |
| JP | 2006-036977 A | 2/2006 | |
| JP | 2006-136263 A | 6/2006 | |
| JP | 2006-223152 A | 8/2006 | |
| JP | 2006-289164 A | 10/2006 | |
| JP | 2007-202560 A | 8/2007 | |
| JP | 2007-301472 A | 11/2007 | |
| JP | 2008-054608 A | 3/2008 | |
| JP | 2008-104452 A | 5/2008 | |
| JP | 2008-278825 A | 11/2008 | |
| JP | 2009-183153 A | 8/2009 | |
| JP | 2009-183154 A | 8/2009 | |
| JP | 2009-183805 A | 8/2009 | |
| JP | 2010-17084 A | 1/2010 | |
| JP | 4436429 B1 | 3/2010 | |
| JP | 4764527 B1 | 9/2011 | |
| JP | 4764528 B1 | 9/2011 | |
| WO | 84/03304 A1 | 8/1984 | |
| WO | 95/17517 A1 | 6/1995 | |
| WO | 96/40970 A1 | 12/1996 | |
| WO | 9640970 A1 | 12/1996 | |
| WO | 2009/096060 A1 | 8/2009 | |
| WO | 2009/096062 A1 | 8/2009 | |
| WO | WO 2009/096061 * | 8/2009 | C13K 1/02 |
| WO | WO 2009096062 A1 * | 8/2009 | |
| WO | 2009/124240 A1 | 10/2009 | |
| WO | 2010/038302 A1 | 4/2010 | |
| WO | 2013/082616 A2 | 6/2013 | |
| WO | 2013/083616 A2 | 6/2013 | |

OTHER PUBLICATIONS

English translation of International Search Report of PCT/JP2010/061724, dated Oct. 5, 2010.

"Biomass Ethanol: Up to 80% sachharification is possible," Nikkei Biotechnology & Business, Sep. 2002, p. 50.

Japanese language International Search Report of PCT/JP2010/061724, mailing date Oct. 5, 2010.

Written Opinion of PCT/JP2010/061724.

Written Opinion of PCT/JP2010/061725, date of mailing Oct. 12, 2010.

Japanese language International Search Report of PCT/JP2010/061725, mailing date Oct. 12, 2010.

Indonesian Office Action dated Nov. 7, 2014, issued in IDW-00200902414, w/English translation (corresponds to U.S. Appl. No. 12/438,792) (6 pages).

Indonesian Office Action dated Nov. 14, 2014, issued in IDW-00201102352, w/English translation (corresponds to U.S. Appl. No. 13/121,969) (7 pages).

Kumagai Satoshi et al. "Fractionation and Saccharification of Cellulose and Hemicellulose in Rice Hull by Hot-Compressed-Water Treatment with Two-Step Heating", Journal of the Japan Institute of Energy, Dec. 1, 2003, vol. 83, pp. 776-781, Cited in Notice of Acceptance dated Mar. 4, 2014, issued in Japanese Patent Application No. 2009-252201.

US Final Office Action dated Feb. 13, 2014, issued in U.S. Appl. No. 12/865,273 (26 pages).

Liu, Chaogang, et al., "Continuous Fermentation of Hemicellulose Sugars and Cellulose to Ethanol", International Symposia on Alcohol Fuels, (2005), pp. 1-28 (cited in U.S. Final Office Action dated Feb. 13, 2014, issued in U.S. Appl. No. 12/865,273 ).

U.S. Non-Final Office Action issued Mar. 10, 2014, in U.S. Appl. No. 13/782,545 (27 pages).

Decision of a Patent Grant dated Mar. 4, 2014, issued in JP2009-252201 (corresponding to U.S. Appl. No. 12/443,515), w/English translation (4 pages).

Decision of a Patent Grant dated Mar. 4, 2014, issued in JP2009-245963 (corresponding to U.S. Appl. No. 12/438,792) w/English translation (4 pages).

Australian Notice of Acceptance dated Mar. 17, 2014, issued in Australian patent application No. 2011355013 (corresponding to U.S. Appl. No. 13/578,116) (2 pages).

U.S. Office Action dated Apr. 14, 2014, issued in U.S. Appl. No. 12/443,515 (16 pages).

Genta, "NEDO ni yoru Biomass Energy to Ko Koritsu Tenkan Gijutsu Kaihatsu 1), Suinetsu Bunkaiho to Koso Bunkaiho wo Kumiawaseta Nogyo Zansa to no Cellulose-kei Biomass no Tei Cost Toka Gijutsu no Kaihatsu" Clean Energy, 2010, pp. 11-15, cited in the Australian Notice of Acceptance dated Mar. 17, 2014, which was previously submitted in the IDS on Apr. 30, 2014.

Canadian Office Action dated Mar. 31, 2014, issued in Canadian Patent Application No. 2,750,753 (3 pages) (corresponding to U.S. Appl. No. 13/203,929).

U.S. Final Office Action dated May 22, 2014, issued in U.S. Appl. No. 13/700,753 (40 pages).

U.S. Final Office Action dated Jun. 3, 2014, issued in U.S. Appl. No. 13/203,929 (22 pages).

Genda, M. et al., "Suinetsu Bunkaiho to Koso Bunkaiho o Kumiawaseta Nogyo Zansa to no Cellulose Biomass no Tei Cost Toka Gijutsu no Kaihatsu", Heisei 21 Nendo Biomass Energy Kanren

(56) References Cited

OTHER PUBLICATIONS

Jigyo Seika Hokokukai, Feb. 11, 2010, pp. 55-69, URL, http://www.nedo.go.jp/events/report/FF_00003.html, Cited in JP Office Action dated Oct. 14, 2014.
Lehrburger, E. "Developing biorefineries to produce energy, ethanol and other industrial products", PureVision Technology, Inc., Alternative Energy Conference, Mar. 3, 2005, pp. 1-26, Cited in U.S. Office Action dated Nov. 6, 2014.
U.S. Office Action dated Sep. 30, 2014, issued in U.S. Appl. No. 13/782,545 (43 pages).
U.S. Office Action dated Nov. 6, 2014, issued in U.S. Appl. No. 12/865,273 (27 pages).
Japanese Office Action dated Oct. 14, 2014, issued in Japanese Patent Application No. 2010-154233 (corresponds to U.S. Appl. No. 13/700,753, with English Translation (7 pages).
U.S. Office Action dated Dec. 5, 2014, issued in U.S. Appl. No. 13/121,969.
Canadian Notice of Allowance dated Dec. 5, 2014, issued in corresponding Canadian Patent Application No. 2750754.
Indonesian Office Action dated Oct. 29, 2014, issued in Indonesian Patent Application No. W00201103522 (corresponds to U.S. Appl. No. 13/203,929), w/English translation.
U.S. Notice of Allowance dated Nov. 5, 2014, issued in U.S. Appl. No. 12/443,515.
U.S. Office Action dated Dec. 26, 2014, issued in U.S. Appl. No. 13/132,040.
Canadian Notice of Allowance dated Aug. 22, 2013, issued in Canadian Patent Application No. 2666152.
Canadian Notice of Allowance dated Aug. 22, 2013, issued in Canadian Patent Application No. 2713529.
U.S. Office Action dated Oct. 28, 2013, issued in U.S. Appl. No. 12/443,515.
U.S. Office Action dated Oct. 7, 2013, issued in U.S. Appl. No. 13/700,753.
U.S. Office Action dated Aug. 19, 2013, issued in U.S. Appl. No. 13/578,116.
U.S. Office Action dated Oct. 3, 2013, issued in U.S. Appl. No. 13/782,545.
Arroyo-Lopez, F.N. et al., "Effects of temperature, pH and sugar concentration on the growth parameters of *Saccharomyces cerevisiae*, *S. kudriavzevii* and their interspecific hybrid", International Journal of Food Microbiology, vol. 131, pp. 120-127 (2009).
Turton, L.J. et al., "Effect of Glucose Concentration in the Growth Medium Upon Neutral and Acidic Fermentation End-products of Clostridium Bifermentans, Clostridium Sporogenes and Peptostreptococcus Anaerobius", J. Med. Microbiol., vol. 16, pp. 61-67 (1983).
Dien, B.S. et al., "Fermentation of hexose and pentose sugars using a novel ethanologenic *Escherichia coli* strain", Enzyme and Microbial Technology, vol. 23, pp. 366-371 (1998).
U.S. Non-Final Office Action dated Dec. 17, 2013, issued in related U.S. Appl. No. 13/203,929 (23 pages).
U.S. Non-Final Office Action dated Dec. 16, 2013, issued in related U.S. Appl. No. 13/132,034 (29 pages).
Gregg, D. et al., "Bioconversion of Lignocellulosic Residue to Ethanol: Process Flowsheet Development", Biomass and Bioenergy, 1995, vol. 9, No. 1-5, pp. 287-302, Cited in U.S. Office Action dated Dec. 17, 2013, issued in U.S. Appl. No. 13/203,929.
Canadian Office Action dated Nov. 8, 2013, issued in Canadian Patent Application No. 2,801,383 (2 pages).
Indonesian Notice of Allowance dated Nov. 15, 2013, issued in Indonesian Patent Application No. W-00201002623, w/ English translation, (5 pages).
U.S. Non-Final Office Action dated Jan. 30, 2014 issued in related U.S. Appl. No. 12/438,792 (39 pages).
Canadian Notice of Allowance dated Jan. 13, 2014, issued in Canadian Patent Application No. 2,744,522 (1 page).
U.S. Non-Final Office Action dated Jan. 30, 2014, issued in related U.S. Appl. No. 13/578,116 (22 pages).

U.S. Final Office Action dated Jul. 3, 2014, issued in U.S. Appl. No. 13/578,116 (17 pages).
U.S. Final Office Action dated Aug. 18, 2014, issued in U.S. Appl. No. 13/132,034 (30 pages).
U.S. Final Office Action dated Jun. 13, 2014, issued in U.S. Appl. No. 12/438,792 (26 pages).
U.S. Non-Final Office Action dated Aug. 27, 2014, issued in U.S. Appl. No. 13/132,040 (53 pages).
U.S. Final Office Action dated Jul. 22, 2014, issued in U.S. Appl. No. 12/443,515 (13 pages).
Non-Final Office Action dated Jun. 19, 2015, issued in U.S. Appl. No. 13/700,753 (34 pages).
Final Office Action dated Aug. 6, 2015, issued in U.S. Appl. No. 14/381,511 (14 pages).
Notice of Allowance dated Aug. 19, 2015, issued in U.S. Appl. No. 12/438,792 (12 pages).
Notice of Allowance dated Aug. 12, 2015, issued in U.S. Appl. No. 13/578,116. (48 pages).
Office Action dated Aug. 21, 2015, issued in U.S. Appl. No. 13/203,929. (18 pages).
Notice of Allowance dated Jul. 6, 2015, issued in Indonesian application No. W-00201103522 (counterpart of U.S. Appl. No. 13/203,929) with English translation (4 pages).
International Search Report dated Jul. 3, 2012 issued in International Application No. PCT/JP2012/058460 (corresponds to U.S. Appl. No. 14/381,511).
Written Opinion of the International Searching Authority dated Jul. 3, 2012 issued in International Application No. PCT/JP2012/058460 (corresponds to U.S. Appl. No. 14/381,511).
Decision of a Patent Grant dated Nov. 12, 2013, issued in Japanese Patent Application No. 2013-536355, w/English translation (corresponds to U.S. Appl. No. 14/381,511) (4 pages).
U.S. Office Action dated Apr. 24, 2015, issued in U.S. Appl. No. 14/381,511 (20 pages).
Notice of Allowance and Fee(s) Due dated Feb. 17, 2015, issued in U.S. Appl. No. 13/782,545 (20 pages).
U.S. Office Action dated Mar. 19, 2015, issued in U.S. Appl. No. 13/121,969 (21 pages).
U.S. Office Action dated Mar. 13, 2015, issued in U.S. Appl. No. 13/722,385 (41 pages).
Notice of Allowance and Fee(s) Due dated Apr. 2, 2015, issued in U.S. Appl. No. 13/132,040 (17 pages).
U.S. Office Action dated Mar. 31, 2015, issued in U.S. Appl. No. 12/865,273 (25 pages).
U.S. Office Action dated May 13, 2015, issued in U.S. Appl. No. 12/438,792 (11 pages).
Office Action dated Sep. 25, 2015 issued in co-pending U.S. Appl. No. 13/132,034 (39 pages).
Office Action dated Jul. 10, 2015 issued in Australian application No. AU2012374915 counterpart to U.S. Appl. No. 13/132,034 (in English) (5 pages).
Notice of allowance dated Sep. 30, 2015 issued in Canadian application No. 2,791,665 counterpart to U.S. Appl. No. 13/132,034 (in English) (1 page).
Decision of a Patent Grant dated Nov. 10, 2015 issued in Japan application No. 2010-154233 counterpart to U.S. Appl. No. 13/700,759 (w/ English translation) (5 pages).
Office Action dated Jul. 10, 2015 issued in Australian application No. AU2012374915 counterpart to U.S. Appl. No. 14/381,511 (in English) (5 pages).
Notice of allowance dated Sep. 30, 2015 issued in Canadian application No. 2,791,665 counterpart to U.S. Appl. Nos. 13/578,116 and 13/782,545 (in English) (1 page).
Decision of a Patent Grant dated Nov. 10, 2015 issued in Japan application No. 2010-154233 counterpart to U.S. Appl. No. 13/700,753 (w/ English translation) (5 pages).
Notice of Allowance dated Dec. 21, 2015, issued in co-pending U.S. Appl. No. 14/381,511 (11 pages) (including PTO892 and returned SB08).

(56) References Cited

OTHER PUBLICATIONS

Supplemental Notice of Allowability dated Jan. 8, 2016, issued in co-pending U.S. Appl. No. 14/381,511 (6 pages) (including returned SB08).

Notice of Allowance dated Feb. 3, 2016, issued in co-pending U.S. Appl. No. 13/578,116 (17 pages) (including returned SB08).

Notice of Allowance dated Mar. 14, 2016, issued in co-pending U.S. Appl. No. 13/121,969 (12 pages) (including returned SB08).

Notice of Acceptance dated Mar. 16, 2016, issued in Australian Application No. 2012374915, counterpart to U.S. Appl. No. 14/381,511 (in English; 2 pages).

Notification of Allowance dated Mar. 30, 2016, issued in Indonesian Patent Application No. W-00200902414 (w/ English translation; 4 pages).

Office Action dated Apr. 22, 2016, issued in co-pending U.S. Appl. No. 13/132,034 (31 pages) (including returned SB08).

Office Action dated Apr. 18, 2016, issued in co-pending U.S. Appl. No. 13/722,385 (31 pages) (including returned SB08).

\* cited by examiner

<BIOMASS MATERIAL>  <AFTER HYDROTHERMAL DECOMPOSITION>

US 9,422,519 B2

BIOMASS HYDROTHERMAL DECOMPOSITION SYSTEM AND SACCHARIDE-SOLUTION PRODUCTION METHOD USING BIOMASS MATERIAL

FIELD

The present invention relates to a biomass hydrothermal decomposition system that can efficiently decompose a biomass material, a saccharide-solution production method using a biomass material, and an alcohol production method.

BACKGROUND

Conventionally, a technique for producing ethanol or the like, in which solid-liquid separation is performed after saccharification of biomass such as wood by using diluted sulfuric acid or concentrated sulfuric acid, and a liquid phase is neutralized and used as a raw material for ethanol fermentation, has been practically utilized (Patent Literature 1, Patent Literature 2).

Further, production of chemical industrial raw materials (for example, lactic acid fermentation) using saccharide as a starting material can also be considered.

In this specification, "biomass" represents organisms incorporated in a substance circulatory system of the global biosphere or accumulation of organic matters derived from the organisms (see JIS K 3600 1258).

Sugarcane, corn and the like, which are currently used as alcohol raw materials, are originally used as food and using these edible resources as industrial resources in a long term and in a stable manner is not preferable in view of a life cycle of effective foodstuff.

Therefore, it is an important issue to effectively use cellulose resources such as herbaceous biomass and woody biomass, which are believed to be useful industrial recourses in the future.

Further, in the cellulose resources, the resource component ratio is varied such that the ratio of cellulose is 38% to 50%, that of hemicellulose component is 23% to 32%, and that of lignin component, which is not used as a fermentation raw material, is 15% to 22%. Because industrial researches have been conducted with many unsolved problems, raw materials in the researches are assumed in a fixed manner, and currently there is no disclosure of a technique of a production system with taking the material versatility into consideration.

Originally, because issues of waste and prevention of the global warming are taken into consideration according to a method unfavorable to fermentation feedstock as compared with starch feedstock, there is less point in the production system in which raw materials are considered in a fixed manner. This production system should be widely applicable to general waste materials. Enzymatic saccharification method itself is not efficient at all, and is thought to be an challenge of the future. A saccharification rate by acid treatment has a considerably small value of about 75% (on a component basis capable of being saccharified) due to excessive decomposition of saccharide caused by overreaction. Therefore, the production yield of ethanol is about 25% with respect to the cellulose resources (Non Patent Literature 1, Patent Literature 3).

In the conventional techniques disclosed in Patent Literatures 1 to 3, there has been a phenomenon in which a reaction by-product causes inhibition of enzymatic saccharification to decrease the saccharide yield. Therefore, a hydrothermal decomposition apparatus that removes a substance inhibiting enzymatic saccharification to increase activity of enzyme based on cellulose has been proposed (Patent Literatures 4 and 5).

CITATION LIST

Patent Literatures

Patent Literature 1: Japanese Patent Application National Publication No. H9-507386
Patent Literature 2: Japanese Patent Application National Publication No. H11-506934
Patent Literature 3: Japanese Patent Application Laid-open No. 2005-168335
Patent Literature 4: Japanese Patent Application Laid-open No. 2009-183805
Patent Literature 5: Japanese Patent Application Laid-open No. 2009-183154

Non Patent Literature

Non Patent Literature 1: Nikkei Bio Business, p. 52, September 2002

SUMMARY

Technical Problem

In the hydrothermal decomposition apparatuses in Patent Literatures 4 and 5 mentioned above, biomass and pressurized hot water are fed into countercurrent contact with each other to cause hydrothermal reaction by internal heat exchange. However, since the internal temperature is high, which is 180 to 240° C., and a pressure higher by 0.1 to 0.4 MPa is applied to a saturated vapor of water at respective temperatures, when discharging a biomass solid as it is under an increased pressure to put it under a normal pressure after the reaction, there is a problem that the effluence of nitrogen, for example, which is a pressurized gas, occurs.

Further, a hydrothermal decomposition product discharged from a gas-liquid interface between the pressurized hot water and the pressurized gas in a vertical hydrothermal decomposition apparatus is in a high temperature and high pressure state. As a result, the reaction is promoted, and there is a problem that the excessive decomposition of hot-water dissolved hemicellulose obtained after being dissolved in the hot water accompanying the biomass solid or hot-water insoluble cellulose occurs in a high temperature (180 to 240° C.) range.

In view of the above problems, the present invention provides a biomass hydrothermal decomposition system that can prevent the effluence of a pressurized gas when a biomass solid is discharged after a biomass material is hydrothermally decomposed under a high temperature and high pressure state and can suppress the excessive decomposition of cellulose or hemicellulose in the biomass material to efficiently obtain a valuable product. The present invention also provides a saccharide-solution production method using a biomass material and an alcohol production method.

Solution to Problem

According to an aspect of the present invention, a biomass hydrothermal decomposition system includes: a biomass feeding unit that feeds a biomass material containing cellulose, hemicellulose, and lignin under a normal pressure to put it under an increased pressure; a hydrothermal decomposition unit that hydrothermally decomposes the biomass material by pressurized hot water and dissolves a lignin component and a hemicellulose component in the pressurized hot water; a biomass solid discharging unit that discharges a biomass solid from the hydrothermal decomposition unit; and a slurrying vessel communicating with the biomass solid discharging unit, into which water is injected and the discharged biomass solid is added to obtain a slurried biomass solid.

Advantageously, in the biomass hydrothermal decomposition system, the hydrothermal decomposition unit transports the biomass material fed thereto from a lower side to an upper side in an apparatus body by transportation unit, feeds the pressurized hot water from an upper side different from a feed position of the biomass material into the apparatus body, performs hydrothermal decomposition while bringing the biomass material into countercurrent contact with the pressurized hot water, and transfers a hot-water soluble component into a hot-water effluent, which is pressurized hot water to be discharged, thereby separating the lignin component and the hemicellulose component from the biomass material.

Advantageously, the biomass hydrothermal decomposition system further includes a pH measuring device provided on a downstream of the slurrying vessel, for measuring pH in the slurried biomass solid.

Advantageously, the biomass hydrothermal decomposition system further includes a first solid-liquid separation device provided on the downstream of the slurrying vessel, for removing water from the slurried biomass solid to separate a biomass solid.

Advantageously, the biomass hydrothermal decomposition system further includes a first saccharification tank for saccharifying the biomass solid separated by the first solid-liquid separation device.

Advantageously, the biomass hydrothermal decomposition system further includes a first return line for recycling the water separated by the first solid-liquid separation device to the slurrying vessel.

Advantageously, the biomass hydrothermal decomposition system further includes a second saccharification tank for saccharifying the hot-water effluent from the hydrothermal decomposition unit.

Advantageously, the biomass hydrothermal decomposition system further includes a second saccharification tank for saccharifying the hot-water effluent from the hydrothermal decomposition unit. The water separated by the first solid-liquid separation device is mixed with the hot-water effluent.

Advantageously, the biomass hydrothermal decomposition system further includes an enzyme liquefaction tank for performing enzyme liquefaction by adding an enzyme to the biomass solid separated by the first solid-liquid separation device. An enzyme liquefied product obtained in the enzyme liquefaction tank is used to perform saccharification by an enzyme in the first saccharification tank.

Advantageously, the biomass hydrothermal decomposition system further includes a third saccharification tank for saccharifying the slurried biomass solid.

Advantageously, the biomass hydrothermal decomposition system further includes: a second solid-liquid separation device that separates a solid content from a saccharide solution after the saccharification; and a first water separation device that removes water from a saccharide solution after the solid separation.

Advantageously, the biomass hydrothermal decomposition system further includes a second saccharification tank for saccharifying the hot-water effluent from the hydrothermal decomposition unit.

Advantageously, the biomass hydrothermal decomposition system further includes: a third solid-liquid separation device that separates a solid content from a saccharide solution after the saccharification in the second saccharification tank; and a second water separation device that removes water from the saccharide solution after the solid separation.

Advantageously, the biomass hydrothermal decomposition system further includes a second return line for recycling the water separated by the first water separation device or the second water separation device to either one or both of the slurrying vessel and a cooling unit of temperature adjustment unit of the hydrothermal decomposition apparatus.

Advantageously, in the biomass hydrothermal decomposition system, the water separated by the first water separation device or the second water separation device is made to be pressurized hot water by pressurization and heating unit, and a third return line for recycling the water to the pressurized hot water of the hydrothermal decomposition apparatus is provided.

Advantageously, the biomass hydrothermal decomposition system further includes a biological treatment device in the first return line, the second return line, or the third return line.

According to another aspect of the present invention, a saccharide-solution production method using a biomass material includes: feeding a biomass material containing cellulose, hemicellulose, and lignin under a normal pressure to put it under an increased pressure; hydrothermally decomposing the biomass material using pressurized hot water by a hydrothermal decomposition unit; and dissolving a lignin component and a hemicellulose component in the pressurized hot water; thereafter, adding a biomass solid discharged from the hydrothermal decomposition unit to a slurrying vessel containing water injected therein and communicating with the hydrothermal decomposition unit so as to obtain a slurried biomass solid; then, removing water from the slurried biomass solid; and thereafter, performing enzymatic saccharification of the water-removed biomass solid to produce a saccharide solution.

Advantageously, the saccharide-solution production method using a biomass material, on an upstream of the enzymatic saccharification of the water-removed biomass solid, enzyme liquefaction of the biomass solid is performed.

According to still another aspect of the present invention, a saccharide-solution production method using a biomass material includes: feeding a biomass material containing cellulose, hemicellulose, and lignin under a normal pressure to put it under an increased pressure; hydrothermally decomposing the biomass material using pressurized hot water by a hydrothermal decomposition unit; and dissolving a lignin component and a hemicellulose component in the pressurized hot water; thereafter, adding a biomass solid discharged from the hydrothermal decomposition unit to a slurrying vessel containing water injected therein and communicating with the hydrothermal decomposition unit so as to obtain a slurried biomass solid; and after performing enzymatic saccharification of the slurried biomass solid to obtain a saccharide solution, separating a solid content therefrom, and then removing water therefrom.

According to still another aspect of the present invention, in an alcohol production method, alcohol fermentation is performed using the saccharide solution obtained by the saccharide-solution production method using a biomass material according to any one of the above method so as to produce alcohol.

Advantageous Effects of Invention

According to the present invention, by adding the hydrothermally-decomposed biomass solid into the liquid in the slurrying vessel containing water injected therein, the biomass solid is slurried and liquid seal is achieved. As a result, it is possible to prevent the effluence of the pressurized gas. Thus, the effluence of a pressurizing gas (for example, pressurized nitrogen or the like) is prevented, thereby achieving a reduction in the running cost.

Further, since the biomass solid is added into the liquid, the biomass solid is cooled by the direct heat exchange with the liquid. Therefore, the reaction can be efficiently terminated, thereby suppressing the excessive decomposition of residual hemicellulose, residual lignin, and the main component, cellulose, due to the hot water accompanying the biomass solid. As a result, the generation of the reaction inhibiting component can be suppressed, and the recovery rate of the cellulose component can be improved.

DESCRIPTION OF EMBODIMENTS

The present invention will be described below in detail with reference to the drawings. The present invention is not limited by the embodiments. In addition, constituent elements in the following embodiments include those that can be easily assumed by persons skilled in the art or that are substantially equivalent.

First Embodiment

The biomass hydrothermal decomposition system according to the present invention will be described with reference to the drawings.

Figure 1:
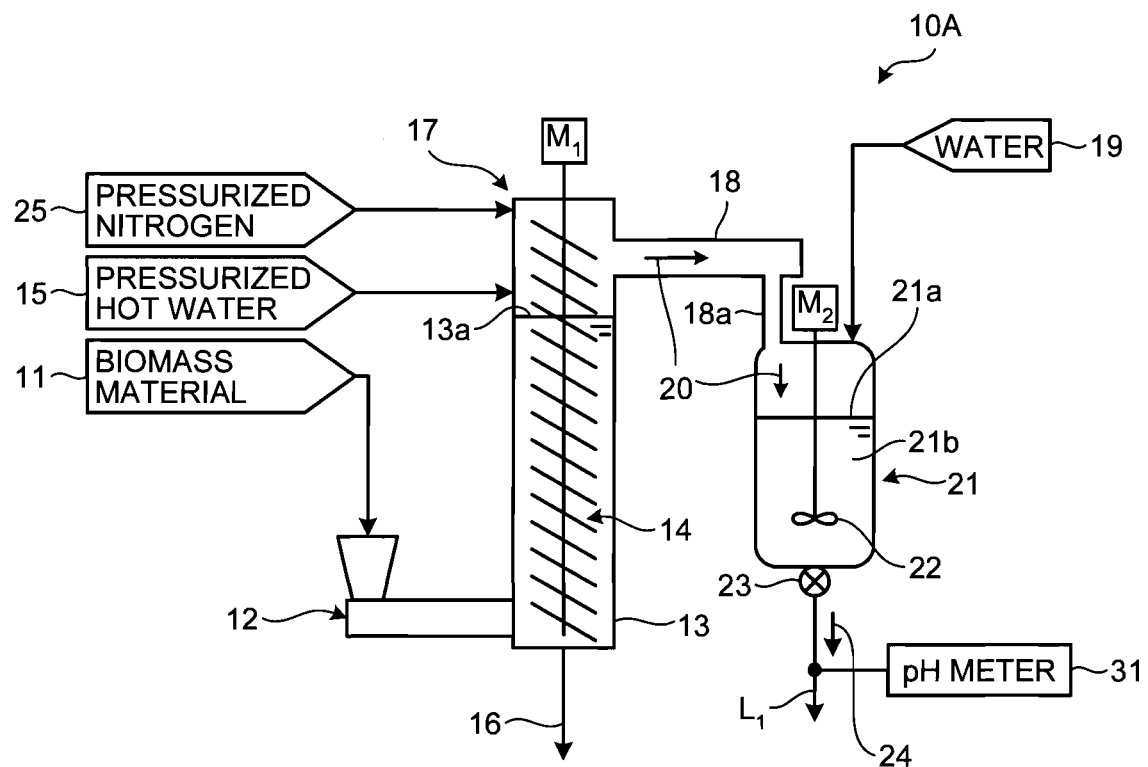
FIG. 1 is a schematic diagram of a biomass hydrothermal decomposition system according to a first embodiment.

FIG. 1 is a schematic diagram of a biomass hydrothermal decomposition system according to a first embodiment. As shown in FIG. 1, a biomass hydrothermal decomposition system 10A according to the present embodiment includes: a biomass feeding unit 12 that feeds a biomass material 11 containing cellulose, hemicellulose, and lignin under a normal pressure to put it under an increased pressure; a hydrothermal decomposition unit 17 that hydrothermally decomposes the biomass material 11 by pressurized hot water (hereinafter, referred to also as "hot water") 15 and dissolves a lignin component and a hemicellulose component in the pressurized hot water 15; a biomass solid discharging unit 18 that discharges a biomass solid 20 from the hydrothermal decomposition unit 17; a slurrying vessel 21 communicating with the biomass solid discharging unit 18, into which water 19 is injected and the discharged biomass solid 20 is added to obtain a slurried biomass solid 24; and a discharge unit 23 that discharges the slurried biomass solid 24 under an increased pressure to put it under a normal pressure.

As the above-described hydrothermal decomposition unit, a known hydrothermal processing device that decomposes the biomass material 11 under a high temperature and high pressure condition can be used. While one example of the hydrothermal decomposition apparatus will be described using FIG. 1, the present invention is not limited to this apparatus.

As shown in FIG. 1, in the hydrothermal decomposition apparatus according to the present embodiment, the biomass material 11 fed to the hydrothermal decomposition unit 17 is transported from a lower side to an upper side in an apparatus body 13 by first screw means 14 which is transportation means; the pressurized hot water 15 is fed from an upper side different from the feed position of the biomass material 11 into the apparatus body 13; hydrothermal decomposition is performed while bringing the biomass material 11 into countercurrent contact with the pressurized hot water 15; and hot-water soluble components (a lignin component and a hemicellulose component) are transferred into a hot-water effluent 16, which is pressurized hot water to be discharged, thereby separating the lignin component and the hemicellulose component from the biomass material 11.

Herein, screw means is exemplified as the transportation means in the present embodiment. However, the transportation means is not limited to the screw means as long as it is capable of transporting a biomass solid from the lower side to the upper side.

The water 19 to be added to the slurrying vessel 21 is only required to be in a liquid state under a pressure in the system in order to achieve liquid seal for the purpose of preventing the leakage of pressurized nitrogen 25 for pressurization. In order to suppress the excessive decomposition (the decomposition starting temperature is about 140° C. to 180° C.) of hemicellulose in water contained in the biomass solid 20, the temperature of the biomass solid 20 and the temperature of the water 19 to be injected in accordance with the capacity of the slurrying vessel 21 may be suitably set so as to decrease the liquid temperature in the slurrying vessel 21 to be 140° C. or less. As the water 19, water typically used within the range of 0° C. to 60° C., for example, (for example, cooling tower water or chiller water), or the like, can be used. As will be described later, water in the system can be circulated for reuse.

In FIG. 1, reference numeral 18a denotes a passage communicating with the biomass solid discharging unit 18 and the slurrying vessel 21, reference numeral 22 denotes stirring means for stirring the inside of the slurrying vessel 21, reference numeral 13a denotes the gas-liquid interface of the hydrothermal decomposition unit 17, reference numeral 21a denotes the gas-liquid interface of the slurrying vessel 21, reference letter $L_1$ denotes a discharge line, reference letter $M_1$ denotes a motor for driving the first screw means 14, and reference letter $M_2$ denotes a motor for driving the stirring means 22.

Figure 8:
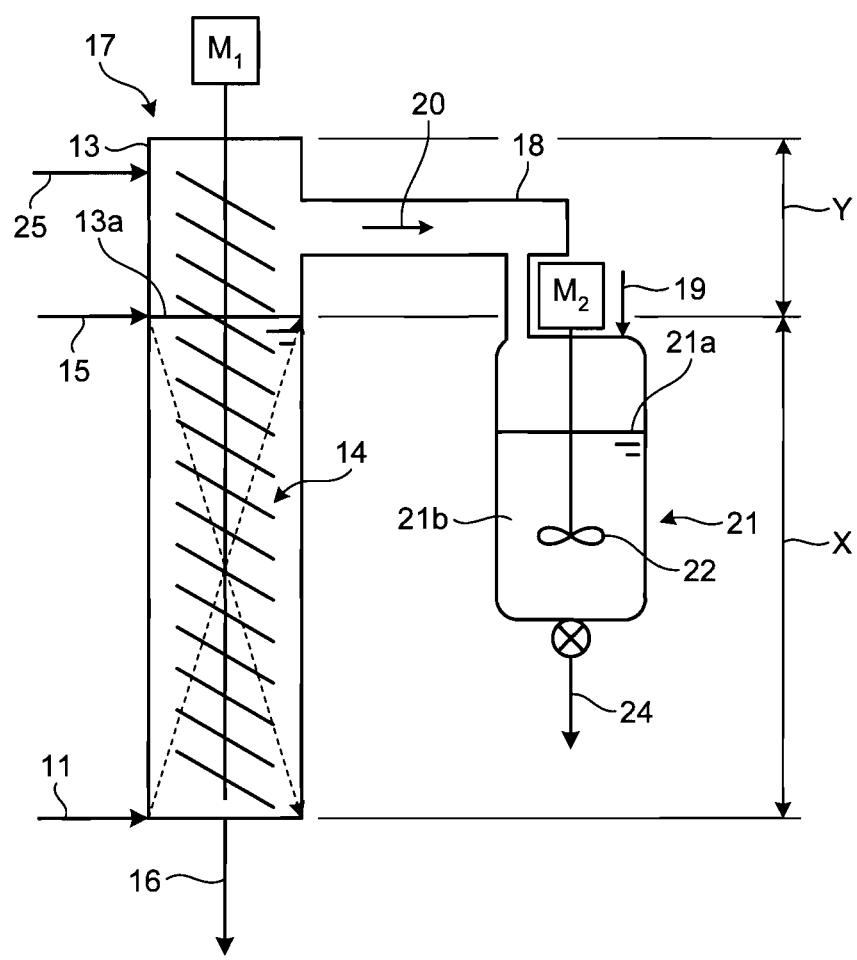
FIG. 8 is a pattern diagram of a vertical hydrothermal decomposition apparatus that hydrothermally decomposes biomass by hot water.
Figure 9:
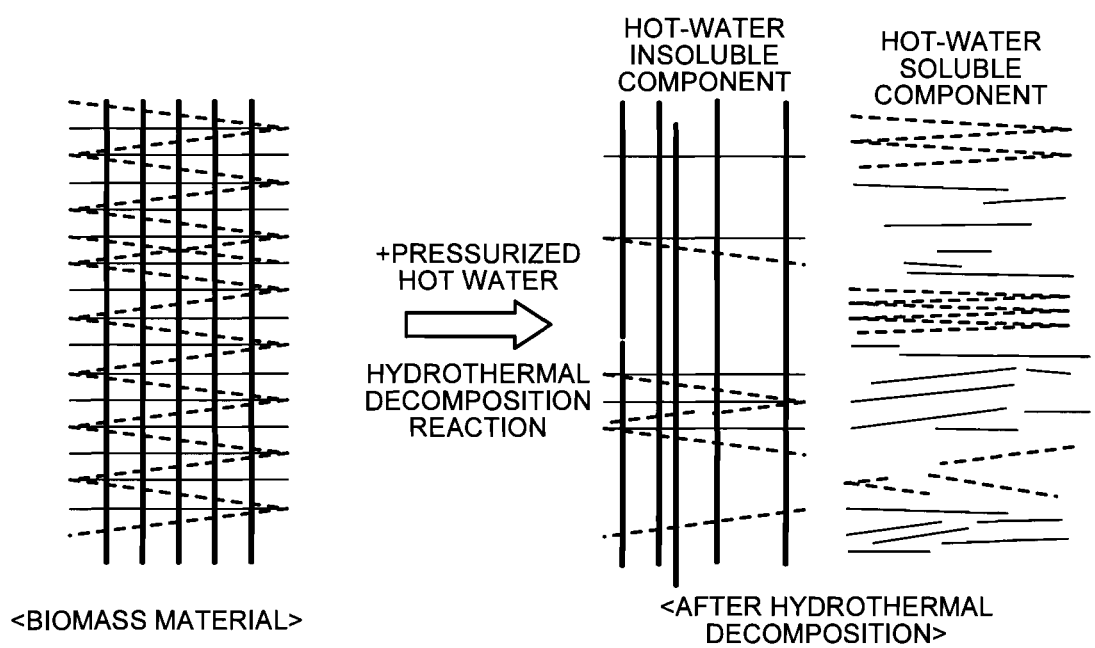
FIG. 9 is a diagram showing how biomass is decomposed by hot water.
Figure 9:
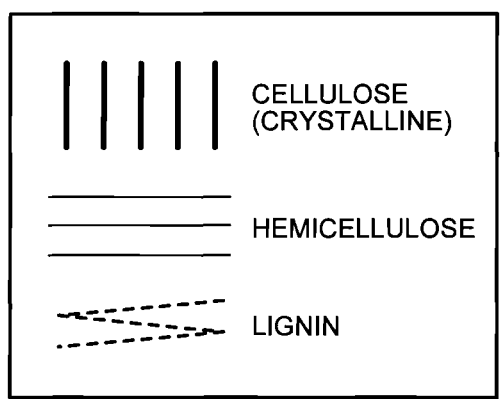

An outline of hydrothermal decomposition of the biomass material 11 by the hydrothermal decomposition unit 17 will be described. FIG. 8 is a pattern diagram of a vertical hydrothermal decomposition apparatus that hydrothermally decomposes biomass by hot water. FIG. 9 is a diagram showing how biomass is decomposed by hot water.

The biomass material 11 and the pressurized hot water 15 are fed to the hydrothermal decomposition unit 17 so as to come into countercurrent contact with each other, and hydrothermal reaction therebetween is caused by internal heat exchange. In FIG. 8, a countercurrent contact zone X and a non-countercurrent contact zone Y are shown. Since a high temperature and high pressure state is kept also in the non-countercurrent contact zone Y, the hydrothermal decomposition reaction of the biomass solid 20 progresses also in the non-countercurrent contact zone Y, thereby possibly resulting in excessive decomposition.

As shown in FIG. 8, the vertical hydrothermal decomposition apparatus feeds the biomass material (a solid form) 11 from the lower side into the apparatus body 13, transfers the biomass material upward by the first screw means 14 provided therein, and drops the biomass solid (a hot-water insoluble component) 20 from the upper side into liquid 21b in the slurrying vessel 21 containing the water 19 injected therein through the biomass solid discharging unit 18.

By providing the slurrying vessel 21 containing the water 19 injected therein as described above, the biomass solid 20 can be cooled efficiently and continuously by direct heat exchange without the leakage of the pressurized nitrogen 25. Thus, it is possible to terminate the hydrothermal decomposition reaction, and it is therefore possible to suppress the hydrothermal decomposition reaction in areas other than the countercurrent contact zone X.

As shown in FIG. 9, the biomass (cellulose material) material 11 contains, in addition to cellulose, hemicellulose and lignin. Specifically, the biomass material 11 has a structure such that cellulose is bundled by hemicellulose with lignin bonding thereto.

After the hydrothermal decomposition, biomass is separated into a hot-water insoluble component (solid) and a hot-water soluble component. The hot-water insoluble component is mainly cellulose (the material of C6 saccharide), and the hot-water soluble component is mainly hemicellulose (the material of C5 saccharide). These are respectively saccharified by enzymes so as to obtain saccharide.

Thus, the biomass material 11 is hydrothermally decomposed by the pressurized hot water 15 in a high temperature (180 to 240° C.) range, and hemicellulose is dissolved on a hot water and lignin is also decomposed and dissolved on the hot water side. As a result, hemicellulose and the like are dissolved on the hot water side.

Hot-water dissolved hemicellulose obtained after being dissolved in hot water causes excessive decomposition in the high temperature (180 to 240° C.) range.

Since the excessive decomposition of hemicellulose causes a reduction in the yield of hemicellulose to be the material of C5 saccharide, it is necessary to suppress the excessive decomposition of hot-water dissolved hemicellulose.

Moreover, the mixing of the excessive decomposition product in hot water becomes a reaction inhibiting factor in a saccharification process by enzymes and a fermentation process such as alcohol fermentation in facilities on a downstream. Therefore, it is also required to suppress the generation of this inhibitor.

In FIG. 1, the biomass solid discharging unit 18 is provided with second screw means, which is not shown in the figure, and the second screw means discharges the biomass solid 20, which is a hot-water insoluble component and transported from the lower side to the upper side by the first screw means 14, to the slurrying vessel 21 side. Then, the discharged biomass solid 20 is successively dropped in the liquid 21b from the passage 18a and stirred by the stirring means 22 provided in the slurrying vessel 21 so as to be slurried.

The biomass solid 20 dropped in the liquid 21b inside the slurrying vessel 21 is cooled by the direct heat exchange with the liquid 21b, thereby suppressing the excessive decomposition of residual hemicellulose, residual lignin, and the main component, cellulose, due to the hot water accompanying the biomass solid 20.

In a gas atmosphere on the upper side of the gas-liquid interface 13a of the hydrothermal decomposition unit 17, the biomass solid 20 is exposed above the hot-water liquid level (gas-liquid interface 13a) by the first screw means 14. However, due to the presence of the pressurized hot water 15 accompanying the biomass solid 20, the reaction is still in progress under the high temperature and high pressure state. Therefore, by adding the biomass solid 20 into the liquid 21b in the slurrying vessel 21, the reaction can be terminated.

Therefore, such a reaction termination leads to the suppression of the excessive decomposition of residual hemicellulose, residual lignin, and the main component, cellulose. As a result, the recovery rate of cellulose is improved since the excessive decomposition of the cellulose component is suppressed, and the generation of the reaction inhibiting component is suppressed on the downstream side.

Due to the injection of the water 19 into the slurrying vessel 21 and the presence of the liquid 21b therein, liquid seal is accomplished in the gas-liquid interface 13a of the hydrothermal decomposition unit 17 and in the gas-liquid interface 21a of the slurrying vessel 21, thereby preventing the leakage of the pressurized nitrogen 25 which is a pressurizing gas. As a result, loss caused by the gas leakage is eliminated, and it is therefore possible to achieve a substantial reduction in the running cost of the pressurizing gas. Note that the slurrying vessel 21 is provided with a safety valve and an input passage of the pressurized nitrogen 25 which are not shown in the figure.

By slurrying the biomass solid 20, fluidization is obtained and the discharge means for discharging the biomass solid 20 from the slurrying vessel 21 to the outside can be simplified. That is, if the biomass solid 20 is kept in a high temperature state, it is necessary to use an expensive material, for example, as the material for the discharge means. However, since the biomass solid 20 is cooled in the slurrying vessel 21, an inexpensive stainless steel, plastic, or the like, can be employed as the material for the discharge unit 23 provided on the discharge side. As the discharge unit 23, a rotary feeder, a flow control valve, or the like, can be used, for example.

Since a biomass solid has a large porosity and a small bulk density, the handling thereof in a solid state is troublesome. However, by slurrying the biomass solid, a reduction in volume is achieved, and the handling thereof therefore becomes easier.

That is, before added to the liquid 21b, the biomass solid 20 is in the form of a cake, has a large porosity due to its large percentage of the pressurizing gas, and has a small bulk density which is 0.5 g/cc or less. By slurrying the biomass solid 20, the void space is reduced, thereby achieving a reduction in volume.

Further, by slurrying the biomass solid 20, fluidization is obtained, and the handling thereof in processes thereafter therefore becomes easier.

Particularly, in the saccharification process, since it is an enzymatic reaction, the biomass solid needs to be cooled to a predetermined temperature or less (for example, 60° C. or less). Then, if biomass in a solid state is cooled, the heat exchange efficiency is not favorable, thereby requiring large heat exchange means. By slurrying the biomass solid, however, favorable cooling efficiency is obtained, thereby eliminating the need for large heat exchange means.

Indirect cooling means for cooling the inside of the slurrying vessel 21 may be provided.

Although the slurrying vessel 21 is provided with the stirring means 22, the present invention is not limited thereto. For example, the stirring may be performed by circulation means by a pump, or the like.

In the present embodiment, a pH meter 31 is provided in the discharge line $L_1$ of the slurried biomass solid 24 discharged from the slurrying vessel 21.

By providing the pH meter 31, it is possible to check the presence or absence of organic acid remained in the slurried biomass solid 24.

Accordingly, it is possible to monitor the occurrences of organic acid (for example, acetic acid or the like) generated by hydrothermal decomposition.

As a result of monitoring pH by the pH meter 31, if a small pH value is obtained in the slurried biomass solid 24, it is determined that organic acid such as acetic acid has been generated. Then, the temperature control for the pressurized hot water of the hydrothermal decomposition unit 17 may be performed.

The control of the hydrothermal decomposition reaction may be performed by measuring pH by the pH meter 31 and controlling the feed amount of the pressurized hot water.

Other control methods of the hydrothermal decomposition unit 17 based on pH include: a method for controlling the hydrothermal decomposition reaction by the control of the feed amount of the biomass material 11 (reaction time); a method for controlling the hydrothermal decomposition reaction by the control of the conveying rate of the biomass material 11 by the first screw means 14 (reaction time); a method for controlling the hydrothermal decomposition reaction by the control of a liquid level of the gas-liquid interface 13a in the apparatus body 13 (reaction time); a method for controlling the hydrothermal decomposition reaction by the control of the discharge amount of the hot-water effluent 16 (reaction time), and the like.

The biomass to be fed to the hydrothermal decomposition unit 17 is not particularly limited. The biomass is defined as organisms incorporated in a substance circulatory system of the global biosphere or accumulation of organic matters derived from the organisms (see JIS K 3600 1258). In the present invention, it is particularly preferable to use cellulose resources such as woods, for example, hardwood plants, and herbaceous biomass, agricultural waste, food waste, or the like.

The particle diameter of the biomass material 11 is not particularly limited. However, it is preferred to mill the biomass material 11 into those with a size of 5 millimeters or less.

In the present embodiment, before feeding the biomass, for example, a mill may be used as a pre-processing device to perform pre-processing. Further, biomass can be cleaned by a cleaning device.

For example, when hull or the like is used as the biomass material 11, it can be fed as it is to the biomass feeding unit 12 without milling.

It is preferred that the reaction temperature in the hydrothermal decomposition unit 17 is in a range from 180 to 240° C., and more preferably from 200 to 230° C.

This is because hydrothermal decomposition rate is low at a low temperature of less than 180° C., and a long decomposing time is required. Therefore, this leads to an increase in size of the apparatus, which is not preferable. On the other hand, at a temperature exceeding 240° C., the decomposition rate becomes excessive, transfer of the cellulose component from a solid phase to a liquid phase increases, and excessive decomposition of hemicellulose saccharides is promoted, which is not preferable.

The hemicellulose component dissolves at about 140° C., cellulose dissolves at about 230° C., and the lignin component dissolves at about 140° C. However, it is preferred that cellulose be left on the solid phase, and the temperature be set to a range from 180° C. to 240° C., at which the hemicellulose component and the lignin component can maintain a sufficient decomposition rate.

As a reaction pressure, it is preferred that a pressure higher by 0.1 to 0.5 MPa be applied to a saturated vapor pressure of water at respective temperatures of the reaction temperature (180 to 240° C.) of the apparatus body 13.

It is also preferred that a reaction time be equal to or shorter than 20 minutes, and preferably, from 3 to 10 minutes. This is because if the reaction time is too long, the rate of excessive decomposition product increases, which is not preferable.

As the biomass feeding unit 12 that feeds biomass under a normal pressure to under an increased pressure, as described above, means such as a screw, piston pump, or slurry pump can be mentioned.

In the present embodiment, the hydrothermal decomposition apparatus is a vertical apparatus. However, the present invention is not limited thereto, and a gradient-type hydrothermal decomposition apparatus having the gas-liquid interface 13a can be used.

The reason why the hydrothermal decomposition apparatus is the gradient type or vertical type is that gas generated in the hydrothermal decomposition reaction, gas brought into the material, and the like, can quickly escape from above, which is preferable. Further, because the decomposition product is extracted by the pressurized hot water 15, the concentration of the extracted product increases from the upper side toward the lower side, which is preferable in view of the extraction efficiency.

As described above, according to the present embodiment, after the biomass material is decomposed into a cellulose-based component and a hemicellulose component under a solid-liquid contact state, the biomass solid, which is the decomposition product, is added into the liquid injected in the slurrying vessel so as to obtain the slurried biomass solid. The liquid seal is also achieved, so that it is possible to prevent the effluence of the pressurized gas. Thus, the effluence of pressurizing gas (for example, pressurized nitrogen or the like) is prevented, thereby achieving a substantial reduction in the running cost.

Second Embodiment

A biomass hydrothermal decomposition system according to another embodiment of the present invention will be described with reference to the drawing. Elements identical to those in the biomass hydrothermal decomposition system according to the first embodiment are denoted by like reference letters or numerals and explanations thereof will be omitted.

Figure 2:
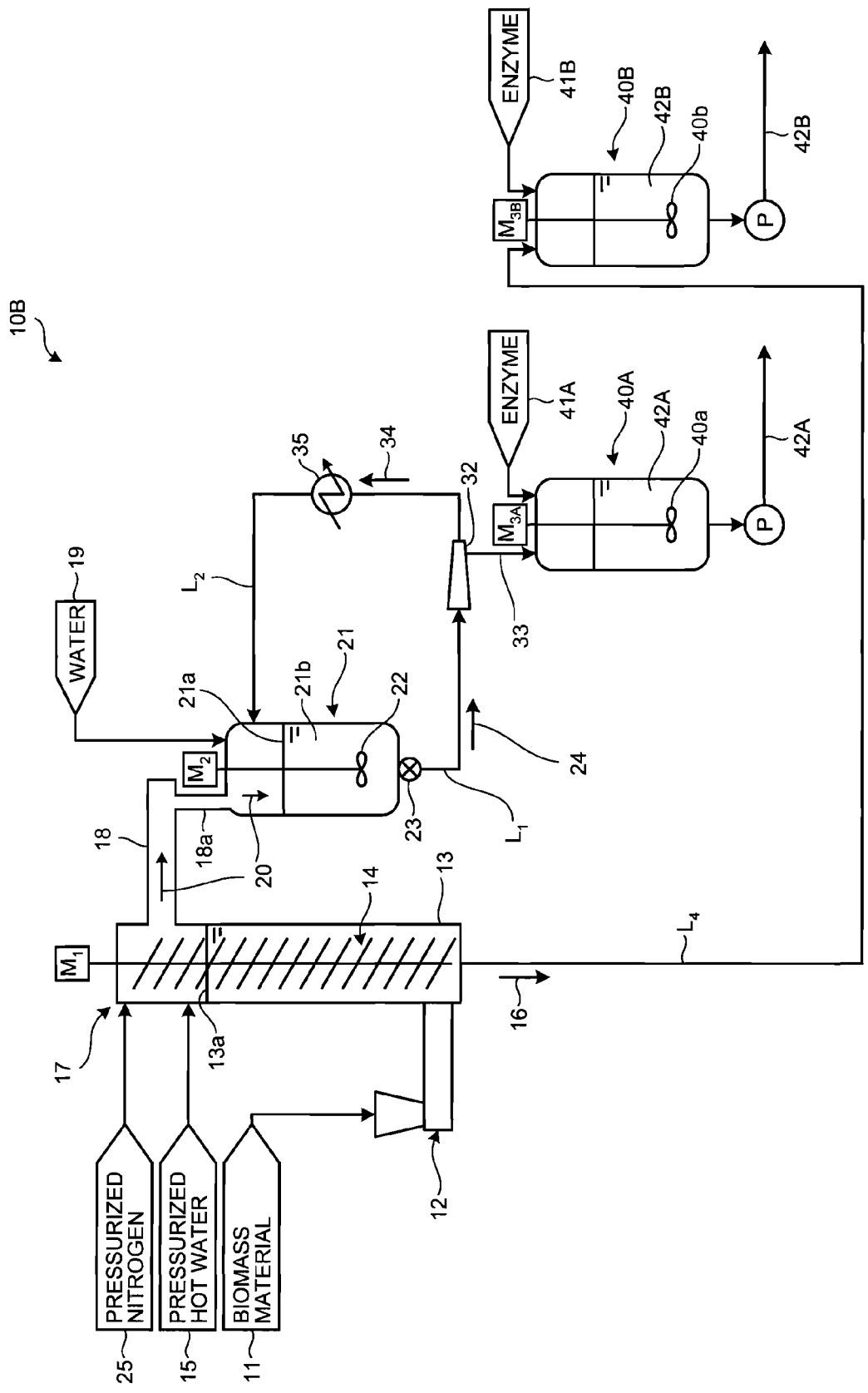
FIG. 2 is a schematic diagram of a biomass hydrothermal decomposition system according to a second embodiment.

FIG. 2 is a schematic diagram of a biomass hydrothermal decomposition system according to a second embodiment.

As shown in FIG. 2, a biomass hydrothermal decomposition system 10B further includes in the biomass hydrothermal decomposition system 10A according to the first embodiment: a first solid-liquid separation device 32 that separates a biomass solid 33 and water 34 and is provided in the discharge line $L_1$ for the slurried biomass solid 24 discharged from the slurrying vessel 21; a first saccharification tank 40A for saccharifying the biomass solid 33 separated by the first solid-liquid separation device 32 by using an enzyme 41A; and a second saccharification tank 40B for saccharifying the hot-water effluent 16 discharged from the hydrothermal decomposition unit 17 by using an enzyme 41B. The biomass solid 33 is saccharified to obtain a sugar solution (C6 saccharide) 42A, and the hot-water effluent 16 is saccharified to obtain a saccharide solution (C5 saccharide) 42B. The water 34 separated by the first solid-liquid separation device 32 is returned to the slurrying vessel 21 through a first return line $L_2$, and the first return line $L_2$ may be provided with a cooler 35 as necessary.

In FIG. 2, reference numerals 40a and 40b denote stirring means, and reference letters $M_{3A}$ and $M_{3B}$ denote motors for driving the stirring means 40a and 40b, respectively.

The first solid-liquid separation device 32 removes the water 34 containing a reaction inhibiting substance to obtain the biomass solid 33. By removing the water 34 by the first solid-liquid separation device 32, a desired solid concentration can be obtained. Thus, it becomes possible to adjust a substrate concentration in the saccharification reaction in the first saccharification tank 40A on a downstream. For example, in order to increase a saccharide concentration after saccharification, the water removal rate in the first solid-liquid separation device 32 may be increased to perform saccharification at a higher substrate concentration. In order to perform saccharification or stirring and transportation after saccharification with an improved operability, or in order to increase the saccharification speed, the water removal rate may be lowered to perform saccharification at a lower substrate concentration.

According to the present embodiment, since unnecessary water is removed by the first solid-liquid separation device 32, it is possible to perform saccharification at a higher substrate concentration, thereby increasing the concentration of C6 saccharide.

Moreover, while the water came along from the hydrothermal decomposition unit 17 and contained in the solid contains a substance that inhibits fermentation, and the like, since the water 34 is removed by the first solid-liquid separation device 32, saccharification can be performed with such a substance and the like being removed. As a result, the quality of saccharide is improved.

Further, since the water 34 can be removed, concentration adjustment becomes possible, and the enzyme conditions can be optimized.

Although the process of obtaining C5 saccharide from the hot-water effluent 16 is also described in the present embodiment, when desired to obtain C6 saccharide only, facilities omitting the saccharification (C5 saccharification) of the hot-water effluent 16 may be provided.

Third Embodiment

A biomass hydrothermal decomposition system according to another embodiment of the present invention will be described with reference to the drawing. Elements identical to those in the biomass hydrothermal decomposition system according to the second embodiment are denoted by like reference letters or numerals and explanations thereof will be omitted.

Figure 3:
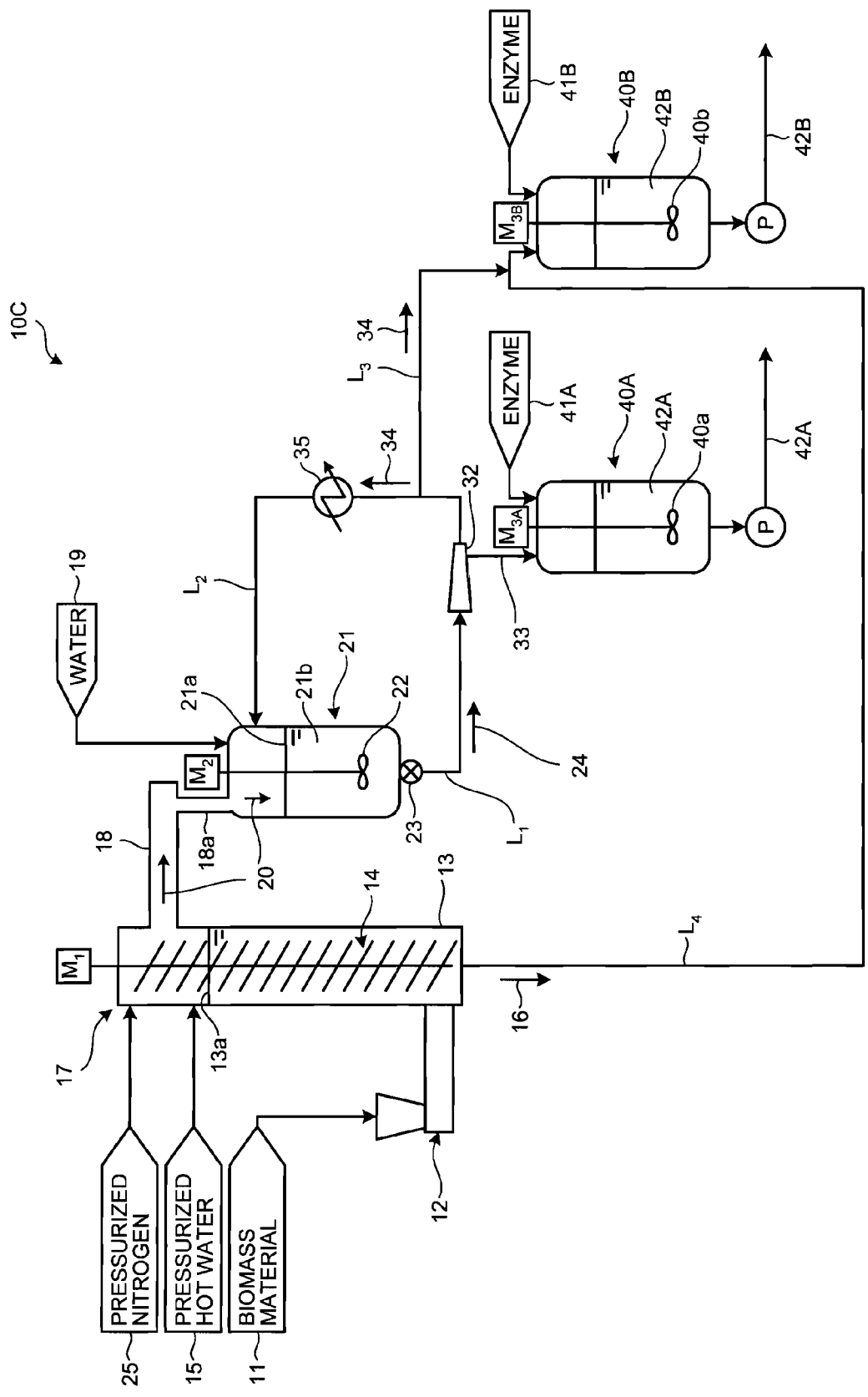
FIG. 3 is a schematic diagram of a biomass hydrothermal decomposition system according to a third embodiment.

FIG. 3 is a schematic diagram of a biomass hydrothermal decomposition system according to a third embodiment.

As shown in FIG. 3, according to a biomass hydrothermal decomposition system 10C, in the biomass hydrothermal decomposition system 10B according to the second embodiment, the water 34 separated from the first solid-liquid separation device 32 is mixed with the hot-water effluent 16 by a feed line $L_3$ to perform saccharification thereafter in the second saccharification tank 40B.

The water 34 separated by the first solid-liquid separation device 32 contains a component to be the material of C5 saccharide such as oligosaccharide which is a hot-water soluble component. Therefore, by performing saccharification in the second saccharification tank 40B on the hot-water effluent 16, it is possible to improve the recovery rate of C5 saccharide.

Fourth Embodiment

A biomass hydrothermal decomposition system according to another embodiment of the present invention will be described with reference to the drawing. Elements identical to those in the biomass hydrothermal decomposition system according to the second embodiment are denoted by like reference letters or numerals and explanations thereof will be omitted.

Figure 4:
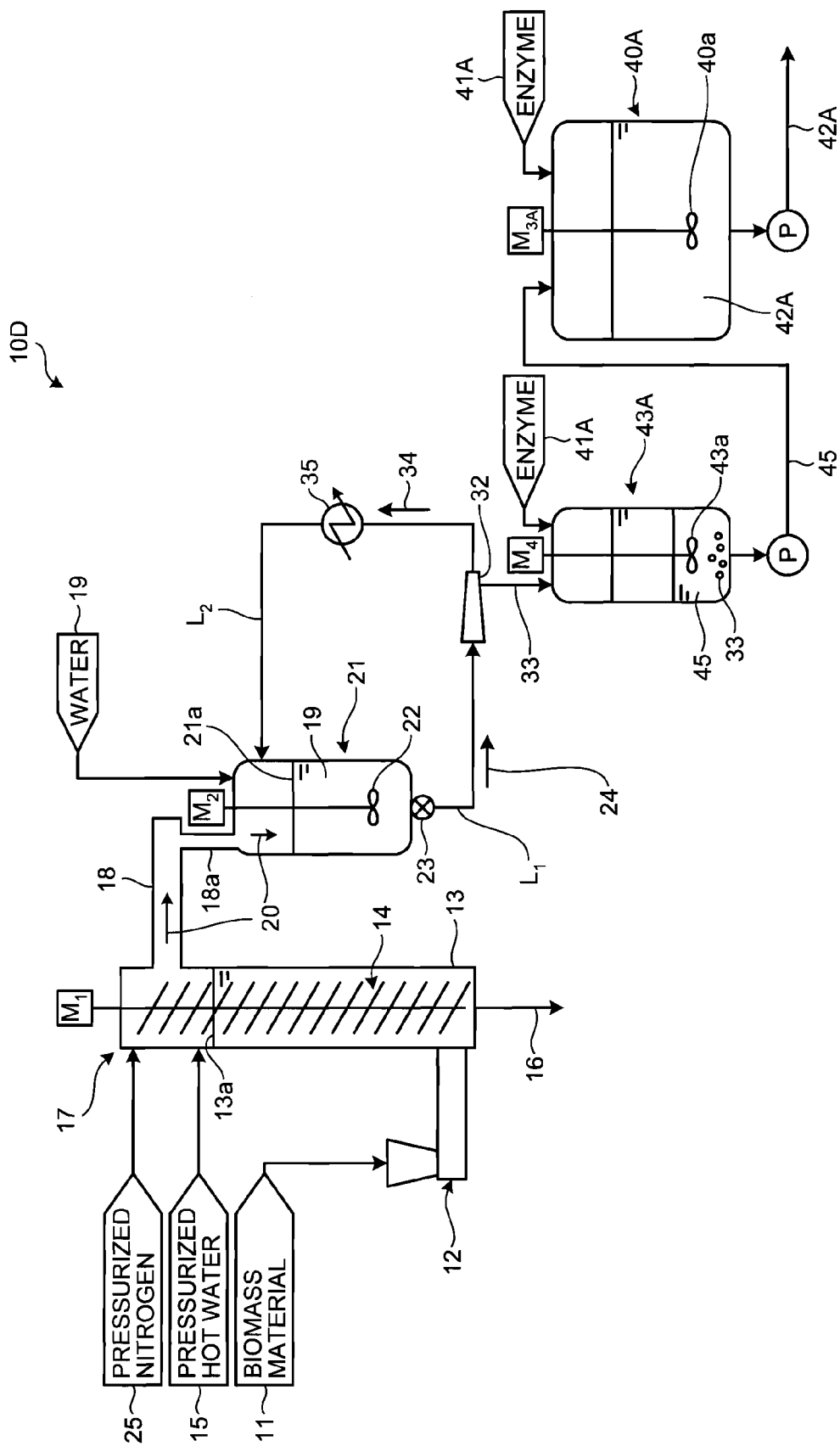
FIG. 4 is a schematic diagram of a biomass hydrothermal decomposition system according to a fourth embodiment.

FIG. 4 is a schematic diagram of a biomass hydrothermal decomposition system according to a fourth embodiment.

As shown in FIG. 4, a biomass hydrothermal decomposition system 10D includes an enzyme liquefaction tank 43A for performing enzyme liquefaction by adding the enzyme 41A to the biomass solid 33 separated by the first solid-liquid separation device 32, in the biomass hydrothermal decomposition system 10B according to the second embodiment.

In the enzyme liquefaction tank 43A, liquefaction is made by hydrolysis of the biomass solid 33 using the enzyme 41A such as cellulase, for example, to produce oligosaccharide, for example. Then, the oligosaccharide, which is an enzyme liquefied product 45, is further hydrolyzed to perform saccharification (monosaccharification: mainly the production of C6 saccharide).

In the present embodiment, a biomass material is fed to the hydrothermal decomposition unit 17 to perform hydrothermal decomposition, thereby continuously obtaining the biomass solid 20. Thereafter, the biomass solid 20 is slurried in the slurrying vessel 21, the biomass solid 33 is then separated therefrom by the first solid-liquid separation device 32, and the enzyme 41A is added thereto to obtain the enzyme liquefied product 45 in the enzyme liquefaction tank 43A. Thereafter, the enzyme liquefied product 45 is introduced into the separately-provided large first saccharification tank 40A to perform batch saccharification for a predetermined reaction time so as to obtain the saccharide solution (C6 saccharide) 42A. If the large first saccharification tank 40A is filled up with liquefied product 45, another large first saccharification tank 40A which is not shown in the drawings may be used to perform the batch process.

Although the amount of the enzyme 41A to be added into the enzyme liquefaction tank 43A is only necessary to be the amount needed to liquefy the biomass solid in the enzyme liquefaction tank 43A with a good operability, the amount of enzyme capable of sufficiently performing saccharification in the enzymatic saccharification tank 40A on a downstream may be added to the enzyme liquefaction tank 43A, for example. Alternatively, placing a great value only on its operability, the amount of the enzyme 41A just enough to perform liquefaction may be added in the enzyme liquefaction tank 43A, and the amount of the enzyme 41A just enough to perform sufficient saccharification may be added in the first saccharification tank 40A on a downstream side.

In the drawing, reference numeral 43a denotes stirring means, and reference letter $M_4$ denotes a motor for driving the stirring means 43a.

In the present embodiment, since the biomass solid 33 is once liquefied in the enzyme liquefaction tank 43A, transportation by a pump, for example, becomes possible, thereby improving the handling ability. Moreover, since liquefaction facilitates stirring, the stirring power of the stirring means $M_{3A}$ of the first saccharification tank 40A can be made small. Further, since enzyme reaction occurs in liquid, the reaction speed is accelerated, thereby contributing to reductions in size and power of the large first saccharification tank 40A and achieving a reduction in the amount of enzyme used.

In the present embodiment, it is preferred that the separated biomass solid 33 be continuously and gradually added to the enzyme liquefied product 45 obtained in the enzyme liquefaction tank 43A. That is, the biomass solid 33 separated by the first solid-liquid separation device 32 is continuously and gradually added into the enzyme liquefied product which has been liquefied in the enzyme liquefaction tank 43A so as to make an adjustment such that the biomass solid, which has a low fluidity, does not exist in the enzyme liquefaction tank 43A as far as possible. Accordingly, stirring capability in the enzyme liquefaction tank 43A and transferability to the enzymatic saccharification tank on a downstream are improved, thereby allowing for a facility operation with a good operability.

In contrast, if the enzyme liquefaction operation is performed when the biomass solid exists in a large amount in the enzyme liquefaction tank 43A, i.e., when the enzyme 41A is added to a large amount of the biomass solid 33 to make liquefaction gradually progress starting from a portion thereof, it will induce a reduction in the production capability and a reduction in the operability in continuous operation.

As described above, according to the present invention, the process up to the enzyme liquefaction tank 43A after continuously adding the biomass material 11 to the hydrothermal decomposition unit 17 can be processed continuously. Thus, it is only necessary to design the capacity or the number of lines of the first saccharification tank 40A for performing sufficient saccharification in accordance with the production capability up to the enzyme liquefaction on the upstream, thereby allowing for a substantial improvement in the facility efficiency and workability thereof.

As described above, as shown in FIG. 2, for example, a saccharide-solution production method using a biomass material according to the present invention includes: feeding a biomass material 11 containing cellulose, hemicellulose, and lignin under a normal pressure to put it under an increased pressure; hydrothermally decomposing the biomass material 11 using pressurized hot water 15 by a hydrothermal decomposition unit 17; dissolving a lignin component and a hemicellulose component in the pressurized hot water 15; thereafter, adding a biomass solid 20 discharged from the hydrothermal decomposition unit 17 to a slurrying vessel 21 containing water 19 injected therein and communicating with the hydrothermal decomposition unit 17 so as to obtain a slurried biomass solid 24; then removing water 34 from the slurried biomass solid 24 by a first solid-liquid separation device 32; and thereafter, performing enzymatic saccharification of a biomass solid 33 from which water has been removed, thereby making it possible to efficiently produce a saccharide solution 42A.

In the above-described saccharide-solution production method using a biomass material, as shown in FIG. 4, for example, enzyme liquefaction is first performed on the upstream of enzymatic saccharification and enzymatic saccharification is then performed by using the enzyme liquefied product 45, thereby improving the productivity of the saccharide solution 42A.

Fifth Embodiment

Figure 5:
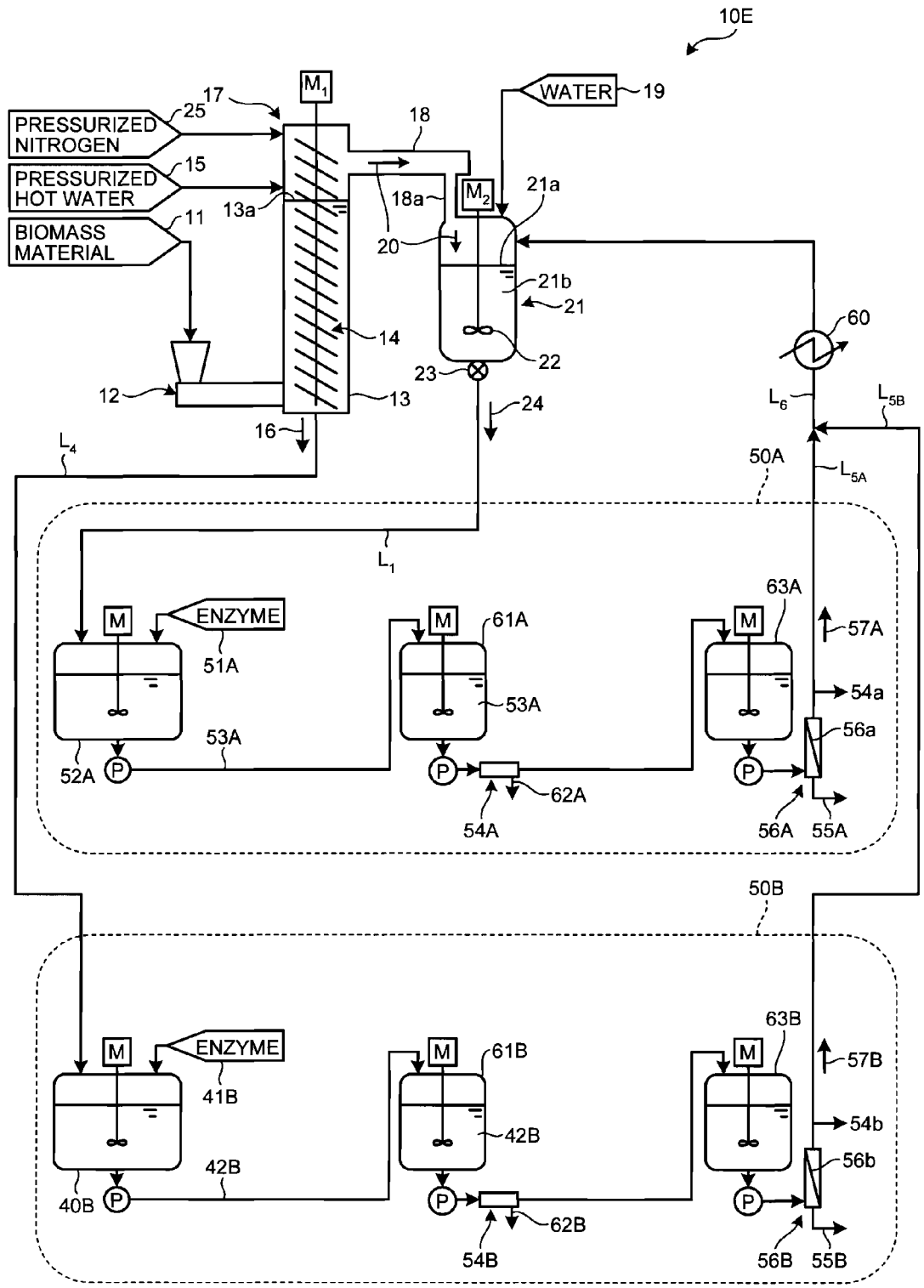
FIG. 5 is a schematic diagram of a biomass hydrothermal decomposition system according to a fifth embodiment.

A biomass hydrothermal decomposition system according to another embodiment of the present invention will be described with reference to the drawing. Elements identical to those in the biomass hydrothermal decomposition system according to the first embodiment are denoted by like reference letters or numerals and explanations thereof will be omitted. FIG. 5 is a schematic diagram of a biomass hydrothermal decomposition system according to a fifth embodiment.

As shown in FIG. 5, a biomass hydrothermal decomposition system 10E includes: a C6 saccharification and saccharide condensation device 50A that performs enzymatic saccharification of the biomass solid mainly containing a cellulose component to obtain hexose (C6 saccharide) or the like and condenses the saccharide; and a C5 saccharification and saccharide condensation device 50B that performs enzymatic saccharification of the hot-water effluent 16 mainly containing a hemicellulose component to obtain pentose (C5 saccharide) or the like and condenses the saccharide, in the biomass hydrothermal decomposition system 10A according to the first embodiment.

The C6 saccharification and saccharide condensation device 50A and the C5 saccharification and saccharide condensation device 50B respectively include: a third saccharification tank 52A for performing enzymatic saccharification of the slurried biomass solid by an enzyme 51A, and the second saccharification tank 40B for performing enzymatic saccharification of the hot-water effluent 16 from the hydrothermal decomposition unit 17 by the enzyme 41B; a second solid-liquid separation device 54A and a third solid-liquid separation device 54B that respectively separate solid contents from a saccharide solution 53A and the saccharide solution 42B after the saccharification; and water separation devices 56A and 56B respectively having reverse osmosis (RO) membranes 56a and 56b that remove water 57A and 57B from the saccharide solutions 53A and 42B separated by the second solid-liquid separation device 54A and the third solid-liquid separation device 54B to obtain condensed saccharide solutions 55A and 55B.

For example, the second solid-liquid separation device 54A and the third solid-liquid separation device 54B may use a screw decanter, a sand filtration device, an MF membrane, or the like, solely or in a combination thereof. As a result, the solid is removed, and the protection of the RO membranes 56a and 56b is therefore achieved. Further, on the preceding stage of the RO membranes 56a and 56b, an ultrafiltration membrane (UF membrane) can be used to protect the RO membranes and enable the recovery of the enzyme, thereby allowing for reuse of the enzyme.

The water separation devices 56A and 56B may employ a loose RO membrane, a nanofiltration membrane (NF membrane), or the like.

A procedure of the processes of the C6 saccharification and saccharide condensation device 50A and the C5 saccharification and saccharide condensation device 50B will be described.

<Enzymatic Saccharification Process>

First, the slurried biomass solid 24 is introduced in the above-described third saccharification tank 52A through the discharge line $L_1$ and the enzyme 51A is added thereto so as to perform saccharification due to enzyme reaction in the enzymatic saccharification process.

On the other hand, the hot-water effluent 16 is introduced in the above-described second saccharification tank 40B through a hot-water effluent feed line $L_4$ and the enzyme 41B is added thereto so as to perform saccharification due to enzyme reaction in the enzymatic saccharification process.

Since the following processes are similar to each other in C6 saccharide and C5 saccharide solid-liquid separation processes, the process of the C6 saccharification and saccharide condensation device 50A will be described.

<Solid-Liquid Separation Process>

The saccharide solution 53A is stored in a first saccharide-solution tank 61A, solid residual liquid 62A such as lignin is then separated by the second solid-liquid separation device 54A, and the saccharide solution 53A is then stored in a second saccharide solution tank 63A.

<Saccharide Condensation Process>

The water 57A is removed from the saccharide solution 53A by the water separation device 56A including the RO membrane 56a to obtain the condensed saccharide solution 55A.

The condensed saccharide solution 55A is turned into various organic materials in a fermentation process which is a subsequent process not shown in the figure.

In the present embodiment, since the slurried biomass solid 24 is used to perform saccharification, saccharification is made at a low substrate concentration, thereby allowing for high-speed saccharification.

Further, such a slurried state enables stirring and transportation, etc., to be performed with a good operability.

Further, since saccharification is made at a low substrate concentration, it is possible to reduce the amount of enzyme used.

Further, the membrane processes using various membranes make it possible to efficiently perform saccharide condensation.

Further, since the separated solid residual liquid 62A (62B) such as lignin has a high calorie, it can be used as a fuel. Further, the solid residual liquid 62A (62B) such as lignin can be employed for an organic fertilizer application or a chemical raw material application (for example, an application as a lignin adhesive).

Further, in the present embodiment, there are provided with second return lines $L_{5A}$ and $L_{5B}$ for recycling the water 57A and 57B separated from the water separation devices 56A and 56B to the slurrying vessel 21.

Further, a cooler 60 is placed in a merged line $L_6$ formed by merging together the second return lines $L_{5A}$ and $L_{5B}$ so as to cool the water to a predetermined temperature, and the cooled water is then returned to the slurrying vessel 21. The cooler 60 may be placed each in the discharge line $L_1$ for the slurried biomass solid 24 and in the hot-water effluent feed line $L_4$ to perform cooling to temperatures desired in the third saccharification tank 52A and the second saccharification tank 40B. In such a case, the cooler 60 in the merged line $L_6$ can be omitted.

Accordingly, the separated water 57A and 57B can be reused, thereby reducing the amount of use of the water 19 separately fed to the slurrying vessel 21.

As described above, as shown in FIG. 5, a saccharide-solution production method using a biomass material according to the present invention includes: feeding a biomass material 11 containing cellulose, hemicellulose, and lignin under a normal pressure to put it under an increased pressure; hydrothermally decomposing the biomass material 11 using pressurized hot water 15 by a hydrothermal decomposition unit 17; dissolving a lignin component and a hemicellulose component in the pressurized hot water 15; thereafter, adding a biomass solid 20 discharged from the hydrothermal decomposition unit 17 to a slurrying vessel 21 containing water 19 injected therein and communicating with the hydrothermal decomposition unit 17 so as to obtain a slurried biomass solid 24; performing enzymatic saccharification of the slurried biomass solid 24 to obtain a saccharide solution 53A; thereafter, separating a solid content therefrom; and then removing water therefrom. Thus, it is possible to efficiently produce a saccharide solution from the biomass material.

Sixth Embodiment

A biomass hydrothermal decomposition system according to another embodiment of the present invention will be described with reference to the drawing. Elements identical to those in the biomass hydrothermal decomposition system according to the fifth embodiment are denoted by like reference letters or numerals and explanations thereof will be omitted.

Figure 6:
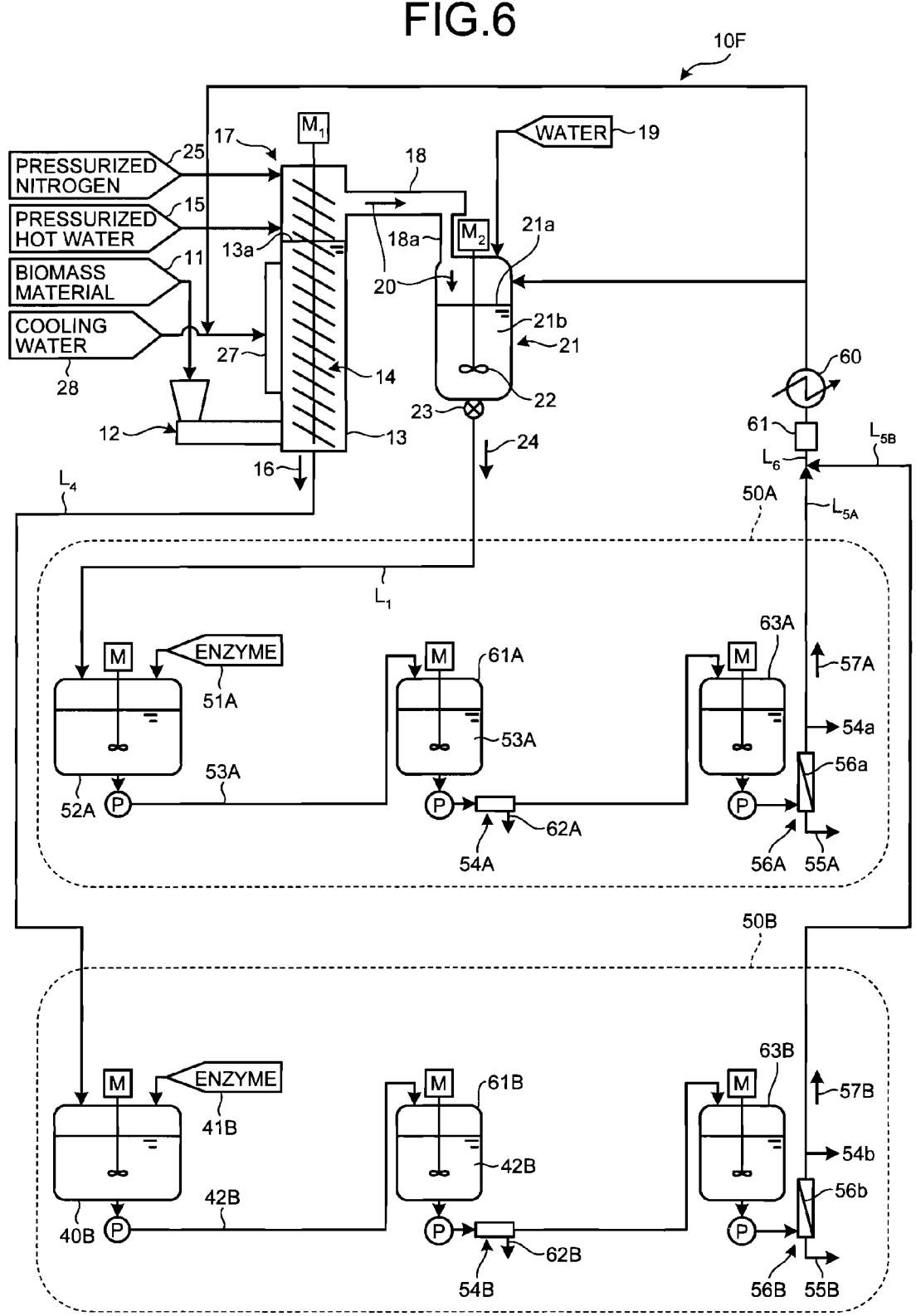
FIG. 6 is a schematic diagram of a biomass hydrothermal decomposition system according to a sixth embodiment.

FIG. 6 is a schematic diagram of a biomass hydrothermal decomposition system according to a sixth embodiment.

As shown in FIG. 6, a biomass hydrothermal decomposition system 10F includes a biological treatment device 61 in the line $L_6$ formed by merging together the second return line $L_{5A}$ and the second return line $L_{5B}$. After the water 57A and 57B is subjected to a biological treatment, the water 57A and 57B is returned to the slurrying vessel 21.

Since the water 57A and 57B separated by the RO membrane 56a includes a reaction inhibiting substance (low-molecular organic compound), the treatment thereof becomes easier by the biological treatment device 61. By using, for example, a methane fermentation biological treatment device as the biological treatment device 61, methane is recovered and can be used as a fuel or the like.

Further, in order to maintain a preferable temperature of the hydrothermal decomposition reaction in the hydrothermal decomposition unit 17, there may be provided with internal temperature maintaining means 27, which is formed extending from an upper side toward one side of the apparatus body 13 of the biomass hydrothermal decomposition unit 17 for keeping a feed temperature (180 to 240° C., for example 200° C.) of the pressurized hot water 15 for a certain period of time and performing a temperature adjustment within the effective reaction zone of hydrothermal decomposition (hydrothermal decomposition zone). Cooling water 28 may be fed to the internal temperature maintaining means 27 so as to adjust the temperature of the hydrothermal decomposition unit. The water treated by the biological treatment device 61 may be merged into the cooling water 28 to be fed to the internal temperature maintaining means 27 for use in the temperature adjustment.

Seventh Embodiment

A biomass hydrothermal decomposition system according to another embodiment of the present invention will be described with reference to the drawing. Elements identical to those in the biomass hydrothermal decomposition system according to the sixth embodiment are denoted by like reference letters or numerals and explanations thereof will be omitted.

Figure 7:
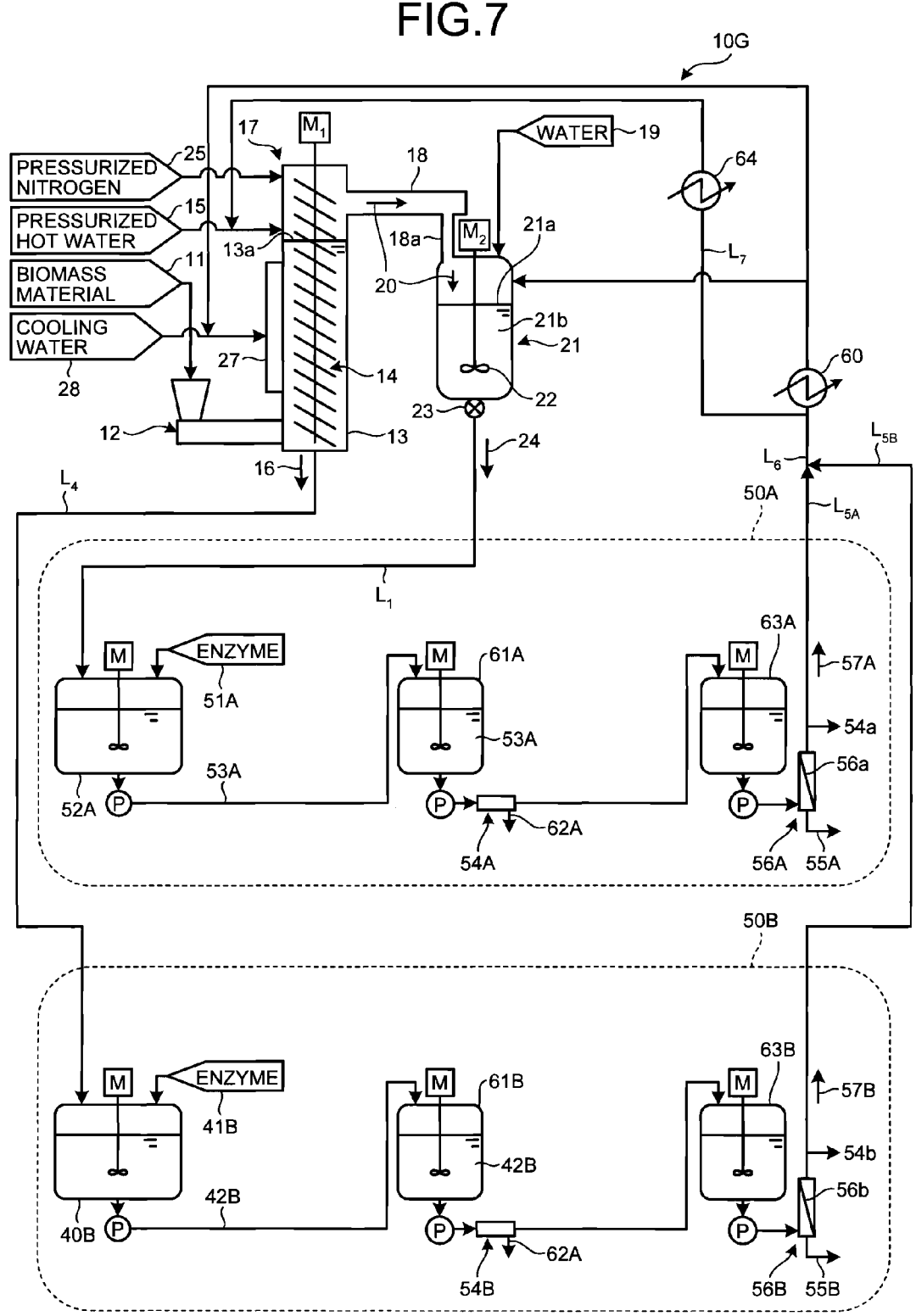
FIG. 7 is a schematic diagram of a biomass hydrothermal decomposition system according to a seventh embodiment.

FIG. 7 is a schematic diagram of a biomass hydrothermal decomposition system according to a seventh embodiment.

As shown in FIG. 7, a biomass hydrothermal decomposition system 10G includes heating means 64 provided in a line $L_7$ branched off from the line $L_6$ formed by merging together the second return line $L_{5A}$ and the second return line $L_{5B}$. Accordingly, the separated water 57A and 57B is heated under an increased pressure and fed for reuse to the hydrothermal decomposition unit 17 as the pressurized hot water 15.

Since the separated water 57A and 57B contains organic acid such as acetic acid, by lowering pH, it becomes possible to reduce the reaction temperature at the hydrothermal decomposition unit 17. Thus, the amount of energy used can be reduced.

In a case where organic acid in the water 57A and 57B is excessive, the water can be reused by providing the biological treatment device 61 as in the sixth embodiment and then performing pressurization and heating thereon.

As described above, according to the biomass hydrothermal decomposition system of the present invention, after the biomass material is decomposed into a cellulose-based component and a hemicellulose component under a solid-liquid contact state, the biomass solid, which is the decomposition product, is added into the liquid provided inside the slurrying vessel so as to obtain the slurried biomass solid. Furthermore, liquid seal is achieved, so that it is possible to prevent the effluence of the pressurized gas. Thus, the effluence of pressurizing gas (for example, pressurized nitrogen or the like) is prevented, thereby reducing the running cost.

By slurrying a biomass solid, the handling thereof becomes easier, which is suitable for the saccharification process thereafter. As a result, it is possible to efficiently produce a saccharide solution (C6 saccharide, C5 saccharide). Further, various organic materials (for example, alcohol, petroleum substitutes, or amino acid) such as LPG, automotive fuel, aircraft jet fuel, kerosene petroleum, diesel oil, various heavy oils, fuel gas, naphtha, ethylene glycol as naphtha decomposition product, lactic acid, alcohol (ethanol and the like), amine, alcohol ethoxylate, vinyl chloride polymer, alkyl aluminum, PVA, vinyl acetate emulsion, polystyrene, polyethylene, polypropylene, polycarbonate, MMA resin, nylon, and polyester, for example, can be efficiently produced from the saccharide solution. Therefore, the saccharide solution derived from biomass can be efficiently used as substitutes of chemical products derived from crude oil, which is a depleting fuel, and as a raw material for producing the substitutes.

Further, since the biomass solid is added in the liquid, the reaction can be efficiently terminated by cooling the biomass solid by the direct heat exchange with the liquid, thereby suppressing the excessive decomposition of residual hemicellulose, residual lignin, and the main component, cellulose, due to the hot water accompanying the biomass solid. As a result, the generation of the reaction inhibiting component can be suppressed and the recovery rate of cellulose can be improved.

INDUSTRIAL APPLICABILITY

As described above, according to the biomass hydrothermal decomposition system of the present invention, when separating a cellulose-based component from a biomass material, slurrying is performed, thereby allowing for efficient discharge thereof. Further, a saccharide solution is produced by using the slurried product, and various organic materials (for example, alcohol, petroleum substitutes, or amino acid) can be efficiently produced from the saccharide solution.

REFERENCE SIGNS LIST

10A to 10G biomass hydrothermal decomposition system
11 biomass material
12 biomass feeding unit
13 apparatus body
14 first screw means
15 pressurized hot water
16 hot-water effluent
17 hydrothermal decomposition unit
18 biomass solid discharging unit
19 water
20 biomass solid
21 slurrying vessel
22 stirring means
23 discharge unit
24 slurried biomass solid
25 pressurized nitrogen

The invention claimed is:

1. A biomass hydrothermal decomposition system comprising:
   a biomass feeding unit that feeds a biomass material containing cellulose, hemicellulose, and lignin under a normal pressure to put it under an increased pressure;
   a hydrothermal decomposition unit that hydrothermally decomposes the biomass material by pressurized hot water and dissolves a lignin component and a hemicellulose component in the pressurized hot water, the hydrothermal decomposition unit including a hot-water effluent outlet from which a hot-water effluent containing the lignin component and the hemicellulose component is discharged;
   a biomass solid discharging unit that discharges a biomass solid from the hydrothermal decomposition unit;
   a slurrying vessel comprising:
      a biomass solid inlet that communicates with the biomass solid discharging unit and introduces the biomass solid;
      a water inlet that introduces water; and
      an outlet that discharges a slurried biomass solid composed of the introduced water and the introduced biomass solid;
   a first saccharification tank that is provided downstream of the slurrying vessel and saccharifies the slurried biomass solid with a first enzyme so as to produce a first saccharide solution;
   a hot-water effluent feed line that communicates with the hot-water effluent outlet of the hydrothermal decomposition unit; and
   a second saccharification tank that saccharifies the hot-water effluent with a second enzyme via the hot-water effluent feed line so as to produce a second saccharide solution,
   wherein the biomass solid inlet is provided at an upper portion of the slurrying vessel, and the outlet is provided at a lower portion of the slurrying vessel, so that the biomass hydrothermal decomposition system is configured to provide a liquid seal between a gas-liquid interface of the slurried biomass solid in the slurrying vessel and a gas-liquid interface of hot water of the hydrothermal decomposition unit, and
   wherein the biomass hydrothermal decomposition system further comprises:
      a first solid-liquid separation device that is provided downstream of the first saccharification tank and separates a first solid residual liquid containing lignin from the first saccharide solution; and
      a second solid-liquid separation device that is provided downstream of the second saccharification tank and separates a second solid residual liquid containing lignin from the second saccharide solution
   wherein the biomass hydrothermal decomposition system further comprises a pH measuring device provided downstream of the slurrying vessel, the pH measuring device measures pH in the slurried biomass solid, and wherein the biomass hydrothermal decomposition system is configured to, on a basis of the measured pH, control at least one of the following:
(i) a feed amount of the pressurized hot water;
(ii) a feed amount of the biomass material;
(iii) a conveying rate of the biomass material by a screw means;
(iv) a liquid level of the gas-liquid interface of the hydrothermal decomposition unit; and
(v) a discharge amount of the hot-water effluent.

2. The biomass hydrothermal decomposition system according to claim 1, wherein
the hydrothermal decomposition unit transports the biomass material fed thereto from a lower side to an upper side in an apparatus body by transportation unit, feeds the pressurized hot water from an upper side different from a feed position of the biomass material into the apparatus body, performs hydrothermal decomposition while bringing the biomass material into countercurrent contact with the pressurized hot water, and transfers a hot-water soluble component into the hot-water effluent, thereby separating the lignin component and the hemicellulose component from the biomass material.

3. The biomass hydrothermal decomposition system according to claim 1, further comprising:
a first water separation device that is provided downstream of the first solid-liquid separation device and removes water from the first saccharide solution; and
a second water separation device that is provided downstream of the second solid-liquid separation device and removes water from the second saccharide solution.

4. The biomass hydrothermal decomposition system according to claim 3, further comprising:
a second return line for recycling the water separated by the first water separation device or a second water separation device to either one or both of the slurrying vessel and a cooling unit of temperature adjustment unit of the hydrothermal decomposition apparatus.

5. The biomass hydrothermal decomposition system according to claim 3, wherein
the water separated by the first water separation device a second water separation device is made to be pressurized hot water by pressurization and heating unit, and a third return line for recycling the pressurized hot water to the pressurized hot water of the hydrothermal decomposition apparatus is provided.

6. The biomass hydrothermal decomposition system according to claim 5, further comprising:
a biological treatment device in the first return line, a second return line, or a third return line, wherein the biological treatment device is a methane fermentation biological treatment device that performs a biological treatment on a reaction inhibiting substance contained in water and recovers methane.

* * * * *